US008288342B2

(12) United States Patent
Ahmed et al.

(10) Patent No.: US 8,288,342 B2
(45) Date of Patent: Oct. 16, 2012

(54) METHODS FOR TREATING VASOMOTOR SYMPTOMS IN CASTRATED PROSTATIC CANCER PATIENTS WITH LOW DOSE CYPROTERONE ACETATE

(75) Inventors: Salah U. Ahmed, New City, NY (US);
Sundeep Sethia, Suffern, NY (US);
Kathleen Reape, Newtown Square, NY (US); Howard Hait, Wilmington, DE (US); Carole S. Ben-Maimon, Merion, PA (US)

(73) Assignee: Teva Women's Health, Inc., Woodcliff Lake, NJ (US)

( * ) Notice: Subject to any disclaimer, the term of this patent is extended or adjusted under 35 U.S.C. 154(b) by 97 days.

(21) Appl. No.: 12/577,600

(22) Filed: Oct. 12, 2009

(65) Prior Publication Data

US 2010/0260860 A1   Oct. 14, 2010

Related U.S. Application Data

(60) Provisional application No. 61/136,893, filed on Oct. 10, 2008.

(51) Int. Cl.
*A61P 5/26* (2006.01)

(52) U.S. Cl. ....... 514/10.2; 424/451; 424/464; 424/489; 514/19.5; 514/178

(58) Field of Classification Search .................. 424/451, 424/464, 489; 514/10.2, 19.5, 178
See application file for complete search history.

(56) References Cited

U.S. PATENT DOCUMENTS

| | | | |
|---|---|---|---|
| 3,895,110 A | | 7/1975 | Itil et al. |
| 4,310,523 A | * | 1/1982 | Neumann ............... 514/178 |
| 4,498,420 A | | 2/1985 | Botterman et al. |
| 4,565,657 A | | 1/1986 | Junghans |
| 5,071,657 A | | 12/1991 | Oloff et al. |
| 5,110,475 A | | 5/1992 | Rössling et al. |
| 5,382,434 A | | 1/1995 | de Haan et al. |
| 5,498,420 A | | 3/1996 | Mentrup et al. |
| 5,723,146 A | | 3/1998 | Rössling et al. |
| 5,955,454 A | | 9/1999 | Merkus |
| 6,165,504 A | * | 12/2000 | Bell ........................ 424/464 |
| 6,613,758 B1 | | 9/2003 | Bell |
| 7,163,699 B2 | | 1/2007 | Besse et al. |
| 7,371,405 B2 | | 5/2008 | Bunick et al. |
| 2001/0041699 A1 | | 11/2001 | Bell |
| 2005/0020552 A1 | | 1/2005 | Aschkenasy et al. |
| 2005/0207990 A1 | | 9/2005 | Funke et al. |
| 2006/0211873 A1 | | 9/2006 | Manosroi et al. |

FOREIGN PATENT DOCUMENTS

DE       2345377 A1    3/1975

OTHER PUBLICATIONS

Barradell, L.B. & Faulds D., "Cyproterone. A review of its pharmacology and therapeutic efficacy in prostate cancer," *Drugs Aging.* 5(1): 59-80, Adis International, New Zealand (1994).
Beckett, A.H. et al., "Improved Hydrodynamics for USP Apparatus 2," *Dissolution Technologies* 3(2): 7-18, Allen Press, United States (1996).
Dawson, N. A. & McLeod D.G., "Dramatic prostate specific antigen decrease in response to discontinuation of megestrol acetate in advanced prostate cancer: expansion of the antiandrogen withdrawal syndrome," *J Urol.* 153(6): 1946-7, Elsevier, United States (1995).
de Voogt, H.J. et al., "Orchidectomy versus Buserelin in combination with cyproterone acetate, for 2 weeks or continuously, in the treatment of metastatic prostatic cancer. Preliminary results of EORTC-trial 30843," *J Steroid Biochem Mol Biol.* 37(6): 965-9, Pergamon Press, England (1990).
Di Silverio, F. et al., "Zoladex vs. Zoladex plus cyproterone acetate in the treatment of advanced prostatic cancer: a multicenter Italian study," *Eur Urol.* 18(suppl 3): 54-61, Elsevier Science, Switzerland (1990).
Eaton, A.C. & McGuire N., "Cyproterone acetate in treatment of post-orchidectomy hot flushes," *The Lancet* 322(8363): 1336-1337, Lancet Publishing Group, England (1983).
Hinkel, A. et al., "Cyproterone acetate in the treatment of advanced prostatic cancer: retrospective analysis of liver toxicity in the long-term follow-up of 89 patients," *Eur Urol.* 30(4): 464-70, Elsevier Science, Switzerland (1996).
International Search Report for International Application No. PCT/US09/60381, United States Patent and Trademark Office, U.S.A., mailed on Dec. 3, 2009.
Kramer, P. et al., In: Murphy G. et al., 3rd Int'l Symposium on Recent Advances in Urological Cancer Diagnosis and Treatment—Proceedings, Paris, France: SCI:3-7 (1992).
Loprinzi, C.L. et al., "Megestrol acetate for the prevention of hot flashes," *N Engl J Med.* 331(6): 347-52, Massachusetts Medical Society, United States (1994).
Mann, M et al., "Glucocorticoidlike activity of megestrol. A summary of Food and Drug Administration experience and a review of the literature," *Arch Intern Med.* 157(15): 1651-6, American Medical Association, United States (1997).
Rabe, T. et al., "Cyproterone acetate: is it hepato- or genotoxic?," *Drug Saf.* 14(1): 25-38, Adis International Ltd., New Zealand (1996).
Ronzoni, G. et al., "Therapy of vasomotor syndrome in the treatment of advanced prostatic cancer: apropos of 37 cases," *Arch Ital Urol Androl.* 70(1):37-40, Masson Italia Periodici, Italy (1998).
The Written Opinion of the International Searching Authority for International Application No. PCT/US09/60381, United States Patent and Trademark Office, U.S.A., mailed on Dec. 3, 2009.
Thorpe, S.C. et al., "A prospective, randomised study to compare goserelin acetate (Zoladex) versus cyproterone acetate (Cyprostat) versus a combination of the two in the treatment of metastatic prostatic carcinoma," *Eur Urol.* 29(1): 47-54, Elsevier Science, Switzerland (1996).

(Continued)

*Primary Examiner* — Ali Soroush
(74) *Attorney, Agent, or Firm* — Fanelli Haag & Kilger PLLC

(57) ABSTRACT

The present invention is directed to methods of treating vasomotor symptoms in castrated prostatic cancer patients in need of treatment, comprising administering about 15 mg or less of cyproterone acetate per day to the patients. The present invention is further directed to dosage forms comprising about 1 mg to about 15 mg of cyproterone acetate and a package comprising a plurality of dosage forms comprising about 1 mg to about 15 mg of cyproterone acetate.

19 Claims, 7 Drawing Sheets

OTHER PUBLICATIONS

Wehbe, T.W. et al., "Prostate-specific antigen response to withdrawal of megestrol acetate in a patient with hormone-refractory prostate cancer," *Mayo Clin Proc.* 72(10): 932-4, Mayo Foundation for Medical Education and Research, United States (1997).

Supplementary European Search Report for EP 09820034.8, European Patent Office, Issued Jul. 11, 2012.

Ronzoni, G. et al., "Hot flushes therapy in advanced prostatic carcinoma" ("Terapia della sindrome vasomotoria nel trattarnento del cancro prostatico avanzato: a proposito di 37 casi"), Arch. It. Urol., LXX, pp. 37-40, 1998.

Bruchovsky, N. et al., "Luteinizing hormone-releasing hormone agonists in prostate cancer," Cancer, vol. 72, 5, pp. 1685-1691, 1993.

Atala, A. et al,, "Diethylstilbestrol in treatment of postorchiectomy vasomotor symptoms and its relationship with serum follicle-stimulating hormone, luteinizing hormone, and testosterone," Urology, vol. 39, 2, pp. 108-110, 1992.

Beckett et al., "Improved Hydrodynamics for USP Apparatus 2," vol. 3, pp. 7-18, 1996, cited in International Search Report.

* cited by examiner

| DISSOLUTION PROFILE (Test Conditions: 0.35 % SLS in 900 mL DI Water, Method: Apparatus II- Paddle, 50 rpm) | | | |
|---|---|---|---|
| Time (min) | 5 mg | 15 mg | 25 mg |
| 0 | 0 | 0 | 0 |
| 15 | 100 | 91 | 92 |
| 30 | 99 | 97 | 100 |
| 45 | 100 | 97 | 102 |
| 60 | 100 | 97 | 103 |
| 75 | 100 | 98 | 104 |

Mean Cyproterone Acetate Concentrations by Treatment and Visit

Mean 15β-OH Cyproterone Acetate Concentrations by Treatment and Visit

METHODS FOR TREATING VASOMOTOR SYMPTOMS IN CASTRATED PROSTATIC CANCER PATIENTS WITH LOW DOSE CYPROTERONE ACETATE

CROSS REFERENCE TO RELATED APPLICATIONS

This application claims the benefit of U.S. Appl. No. 61/136,893, filed Oct. 10, 2008, the contents of which are hereby incorporated by reference in their entireties.

BACKGROUND OF THE INVENTION

1. Field of the Invention

The invention relates to treatments for vasomotor symptoms in surgically or chemically castrated prostatic cancer patients and pharmaceutical dosage forms for use in treating the patients.

2. Background

Prostate cancer is the second most common cancer and the second leading cause of cancer death in American men, with approximately 1 in 6 men diagnosed. As with most cancers, no cure exists for prostate cancer, however, several treatments are available to reduce its progression, including androgen deprivation therapy ("ADT"), prostatectomy, and orchiectomy. The most commonly used treatment is ADT.

Androgens play a key role in the progression of prostate cancer, especially testosterone and dihydrotestosterone. Androgen deprivation can be achieved surgically, by orchiectomy (removal of testicles), or medically by use of drugs. However, ADT has side effects that may decrease a subject's quality of life. One side effect is hot flashes, which can start without warning, last up to 30 minutes, and may vary in frequency from several times a week to more than a dozen episodes per day. Hot flashes are associated with increased pulse rate, anxiousness, irritability, and nausea, and may be experienced as a suddenly occurring feeling of heat that spreads quickly from the face, to the chest and back, then over the rest of the body, and can be accompanied by profuse sweating.

Generally, they are a source of great physical and mental distress to the prostate cancer patient.

The best therapeutic effect on hot flashes is achieved by replacement therapy with sex steroids. However, androgens are contraindicated in male prostate cancer subjects.

The symptoms of hot flashes have been rarely reported in prostate cancer patients treated with estrogens such as diethylstilbestrol ("DES"), or with cyproterone acetate ("CPA") or megestrol acetate ("MA") either alone or in combination with DES. There is no apparent difference in vasomotor hot flash response with respect to whether the primary therapy is surgical or chemical castration, or among patients receiving various formulations of different luteinizing hormone-releasing hormone ("LHRH") agonists. Treatment with pure antiandrogens (such as flutamide) in addition to surgical castration or to LHRH agonist treatment does not appear to significantly influence either the frequency or severity of hot flashes nor the response to treatment. Estrogens such as DES may be effective to decrease hot flashes, but at the risk of gynecomastia and increased cardiovascular morbidity.

MA, a progestational hormone, has been shown to reduce hot flashes in men and women. Various studies of MA, including for treatment of prostate cancer and reduction of hot flashes, have been reported in the literature. See, e.g., Loprinzi et al., *N. Engl. J. Med.* 331: 347-352 (1994); Wehbe, et al., *Mayo Clin. Proc.,* 72: 932-934, 932 (1997); Dawson et al., *J. Urol.* 153:1946-1947 (1995); Mann et al., *Arch. Intern. Med.* 157: 1651-1656 (1997).

CPA, a synthetic 21-carbon hydroxyprogesterone derivative, is disclosed in U.S. Pat. No. 3,234,093, which is incorporated herein by reference. CPA is a steroidal antiandrogenic agent that inhibits the action of adrenal and testicular androgens on prostatic cells, resulting in total androgen blockade. Additionally, due to the antigonadotropic effects of its progestogenic activity, CPA causes a centrally mediated reduction in testicular secretion of androgens. CPA is approved for use in many regions of the world, including Europe, Asia, and South America, as well as in Australia and Canada. It is used as a component of oral contraceptives and in the treatment of acne, seborrhea, hirsutism, precocious puberty, hypersexuality and in the treatment of prostate cancer. The pharmaceutical preparations ANDROCUR® (cyproterone acetate, Berlex Canada CYPROSTAT® (cyproterone acetate, Bayer plc), DIANE® (cyproterone acetate/ethinyl estradiol, Schering Ltd), and DIANETTE® (cyproterone acetate/ethinyl estradiol, Schering Ltd), are CPA-based products. Manufacturers of these products include Schering AG, Berlin, Germany and Berlex, Canada.

Side effects most frequently recorded with CPA treatment relate to the hormonal effects of the drug. These include impotence, inhibition of spermatogenesis and gynecomastia. These reactions are usually reversible upon discontinuation of therapy or reduction in dose. The drug is also associated with rapid falls in serum testosterone levels, which may also produce such central nervous system effects as fatigue, weakness, and headache.

CPA has been investigated for use in treating hot flash symptoms associated with surgical or medical castration. In a double-blind, crossover trial, Eaton and McGuire treated 12 prostate cancer subjects with troublesome post-orchiectomy hot flashes with CPA or placebo. Eaton A C and McGuire N., *Lancet* 8363:1336-1337 (1983). The frequency of hot flashes was significantly reduced during the 3 weeks that CPA (300 mg daily) was given. Ronzoni et al. treated 37 subjects with bothersome hot flashes with CPA or MA. Ronzoni et al., *Arch Ital Urol Androl* 70(1): 37-40 (1998). A therapeutic efficacy of 80% and 70% reduction in hot flashes was observed following administration of CPA and MA, respectively.

Similarly, in a much larger clinical trial in 273 subjects, who had previously undergone orchiectomy, the number of subjects experiencing hot flashes and outbreaks of sweating decreased after treatment with CPA (150 mg daily) compared with placebo. Krämer et al., *Proceedings of the 3rd International Symposium on Recent Advances in Urological Cancer Diagnosis and Treatment*, Paris (1992) June 17-19: pp 3-7. Hot flashes were experienced by 33% of subjects receiving CPA and 61% of subjects receiving placebo, while only 24% of CPA-treated subjects had outbreaks of sweating compared with 47% of placebo-treated subjects. Furthermore, in those subjects receiving CPA who continued to experience hot flashes or sweating, the frequency and severity were decreased. Id. and Barradell et al., *Drugs & Aging* 5/1: 59-80 (1994). In several randomized well-controlled clinical trials in prostate cancer subjects, CPA given in combination with LHRH agonists was associated with a reduction in the percentage of subjects reporting hot flashes. deVoogt et al., *J Steroid Biochem Molec Biol* 37: 965-969 (1990); DiSilverio et al., *Eur Urol* 18 (suppl 3):54-61 (1990); Thorpe et al., *Eur Urol,* 29(1): 47-54 (1996).

The Androcur® Monograph, Berlex Inc., Canada (1997), indicates a general improvement in the subjective assessment of the quality of life in 70% of 367 evaluable patients participating in worldwide studies on CPA. The criteria listed are weight gain and pain relief. The patients considered included ones who received CPA as monotherapy, an estrogen refractory group, and orchiectomized patients. It appears that dosage forms included oral and i.m. injection and that the doses varied. Most patients who received oral CPA were dosed at 200 to 300 mg/day. The lowest oral dose given to orchiectomized patients was indicated to be 100 mg/day.

Dose-related hepatic toxicity in humans has been reported with the prolonged use of CPA. Toxicological studies have revealed, however, that administration of CPA to humans does not pose a serious risk of hepatotoxicity. A retrospective liver toxicity analysis was performed on 89 patients with advanced prostatic cancer who received continuous additional antiandrogenic treatment with 50 mg/day CPA. Hinkel et al., *Eur. Urol.* 30:464-470 (1996).

Moreover, a thorough review on the toxicology of CPA was published by Rabe et al., *Drug Safety*, 14(1):25-38 (1996). In a multi-center surveillance study of long-term CPA use in over 2500 patients, the treatment group included men and women. The men were treated at dosages of either more than 200 mg/day or from 100 to 200 mg/day CPA. No correlation was found between the duration of CPA treatment and the prevalence of liver enzyme elevations.

U.S. Pat. No. 6,165,504 ("the '504 patent") relates to methods for treating hot flashes in a castrated prostatic cancer patient by orally administering from 25 mg to 150 mg CPA per day, preferably from 50 mg to 100 mg CPA per day.

BRIEF SUMMARY OF THE INVENTION

The present invention is directed to a method of treating a vasomotor symptom in a castrated prostatic cancer patient in need of treatment, comprising administering about 15 mg or less of cyproterone acetate per day to the patient.

The present invention is directed to a pharmaceutical dosage form comprising about 1 mg to about 15 mg of cyproterone acetate and pharmaceutically acceptable inactive agents comprising a surfactant in an amount of about 0.1% to about 5.0% (wt/wt), a disintegrant in an amount of about 2% to about 20% (wt/wt), and a filler in an amount of about 20% to about 95% (wt/wt).

The present invention is directed to a pharmaceutical dosage form comprising about 1 mg to about 15 mg of cyproterone acetate and pharmaceutically acceptable inactive agents, wherein the inactive agents comprise sodium lauryl sulfate, crospovidone, anhydrous lactose, and microcrystalline cellulose.

The present invention is directed to a package comprising a plurality of pharmaceutical dosage forms, each dosage form comprising about 1 mg to about 15 mg of cyproterone acetate and a pharmaceutically acceptable inactive agent.

In some embodiments, the patient has at least 3 vasomotor symptoms per day. In some embodiments, the patient has at least 21 vasomotor symptoms per week.

In some embodiments, the treatment reduces the severity of the vasomotor symptom. In some embodiments, the treatment reduces the number of vasomotor symptoms per day.

In some embodiments, the patient is treated for at least 14 days. In some embodiments, the patient is treated for at least 60 days. In some embodiments, the patient is treated for at least 12 weeks. In some embodiments, the patient is treated for at least 6 months. In some embodiments, the patient is treated for 2 to 3 years.

In some embodiments, the patient is treated for at least 14 days consecutively.

In some embodiments, about 1 mg to about 15 mg of cyproterone acetate is administered per day.

In some embodiments, about 5 mg of cyproterone acetate is administered per day. In some embodiments, about 10 mg of cyproterone acetate is administered per day. In some embodiments, about 15 mg of cyproterone acetate is administered per day.

In some embodiments, the patient is a chemically castrated prostatic cancer patient. In some embodiments, the patient is an orchiectomized prostatic cancer patient.

In some embodiments, the administration is oral and is once per day. In some embodiments, the administration is oral and is divided into 2-5 doses per day.

In some embodiments, the cyproterone acetate and the surfactant are present in a ratio of about 1:0.05 to about 0.1:1.

In some embodiments, the pharmaceutical dosage form further comprises a glidant in an amount of about 0.1% to about 3.0% (wt/wt) and a lubricant in an amount of about 0.5% to about 6.0% (wt/wt).

In some embodiments, the cyproterone acetate has a $D_{90}$ of about 25 microns or less.

In some embodiments, greater than 75% of the cyproterone actetate is released in 30 minutes, as tested using a USP Type II Paddle Apparatus containing 0.35% sodium lauryl sulfate in 900 mL water at a paddle speed of 50 rpm.

DETAILED DESCRIPTION OF THE INVENTION

Figure 1:
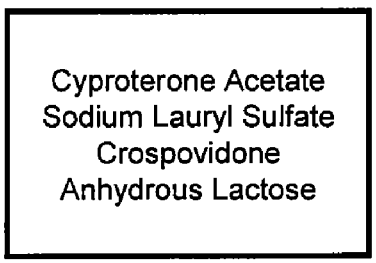
FIG. 1 is a process flow chart representing a process for preparing cyproterone acetate tablets of the present invention.
Figure 1:
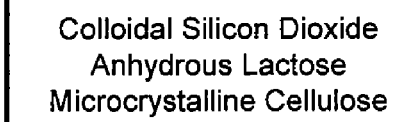
Figure 1:
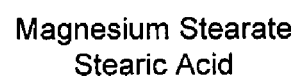

The present invention provides methods for treating vasomotor symptoms in castrated prostatic cancer patients by administering cyproterone acetate. The methods provide a reduction in the number of vasomotor symptoms a patient experiences per day and a reduction in the severity of vasomotor symptoms experienced by the patient or a complete disappearance of vasomotor symptoms.

The present invention is directed to a method of treating a vasomotor symptom in a castrated prostatic cancer patient in need of treatment, comprising administering about 15 mg or less of cyproterone acetate per day to the patient.

As described throughout, 15β-OH cyproterone acetate can be used in place of cyproterone acetate.

In some embodiments, the patient being treated experiences at least 3 vasomotor symptoms per day or at least 21 vasomotor symptoms per week. In some embodiments, the patient experiences 1, 2, 3, 4, 5, 6, 7, 8, 9, 10, 11, 12 or more vasomotor symptoms per day. In accordance with the invention, treatment with cyproterone acetate is for at least a time sufficient to alleviate the vasomotor symptoms. In some embodiments, treatment is provided for at least 14 days. In some embodiments, treatment is chronic. In accordance with the invention, cyproterone acetate can be administered consecutively, i.e., every day, or intermittently, e.g., every other day, once every third day, once every fourth day, once every fifth day, once every sixth day, or once a week.

Castrated prostatic cancer patients, in accordance with the present invention, are those prostate cancer patients who have undergone medical or surgical castration, e.g., bilateral orchiectomy, ablative radiation, or who have undergone or are undergoing chemical castration, e.g., by administration of an LHRH agonist such as Lupron® or Zoladex®. Many patients are additionally undergoing or have undergone pure antiandrogen treatment such as with flutamide.

The present invention is also directed to a method for treating a vasomotor symptom in a castrated prostatic cancer patient, who is currently undergoing treatment with Lupron® and/or flutamide, by administering about 15 mg or less of cyproterone acetate per day. In some embodiments, the cyproterone acetate is administered concurrently with Lupron® and flutamide. In some embodiments, the cyproterone acetate is administered with Lupron® and in place of flutamide.

The terms "treat" and "treatment" refer to therapeutic treatment, wherein the object is to obtain beneficial or desired clinical results. For purposes of this invention, beneficial or desired clinical results include, but are not limited to, a reduction in the number of vasomotor symptoms and/or the severity of vasomotor symptoms, and/or a complete cessation in the occurrence of vasomotor symptoms in the patient.

As used herein, a "vasomotor symptom" refers to a hot flash, a hot flush, a night sweat, sweating, increased pulse rate, anxiousness, irritability, or nausea.

The severity of a vasomotor symptom is defined clinically by the following terms. The term "mild" refers to the sensation of heat without sweating. The term "moderate" refers to the sensation of heat with sweating, wherein a person is able to continue activity. The term "severe" refers to the sensation of heat with sweating, causing a cessation of activity. Guidance for Industry: Estrogen and Estrogen/Progestin Drug Products to Treat Vasomotor Symptoms and Vulvar and Vaginal Atrophy Symptoms—Recommendations for Clinical Evaluation, U.S. Department of Health and Human Services, Food and Drug Administration, Center for Drug Evaluation and Research, January 2003.

A chemically or surgically castrated prostatic cancer patient experiencing a vasomotor symptom is a patient or subject "in need of treatment" in accordance with the present invention.

"Pharmaceutically acceptable" in accordance with the present invention, refers to compositions that are, within the scope of sound medical judgment, suitable for contact with the tissues of human beings and animals without excessive toxicity or other complications commensurate with a reasonable benefit/risk ratio. In some embodiments, the compositions and dosage forms of the present invention are pharmaceutically acceptable.

The treatment term can be consecutive or intermittent, preferably at the discretion of the physician and/or the patient under a doctor's supervision.

In some embodiments, treatment is consecutive, i.e., CPA is taken every day. The term "continuous" or "consecutive," as used herein in reference to "administration," means that the frequency of administration is at least once daily. Note, however, that the frequency of administration can be greater than once daily and still be "continuous" or "consecutive," e.g., twice or even three times daily, as long as the dosage levels as specified herein are not exceeded. In some embodiments, treatment is consecutive for at least 14 days, at least 21 days, at least 30 days, at least 45 days, at least 60 days, at least 12 weeks, at least 6 months, at least 9 months, at least one year, at least 2-3 years, or as long as the patient requires treatment.

"Intermittent treatment," in accordance with the present invention, means that after a treatment with CPA, the patient withdraws from taking the drug for a length of time, and then resumes taking the drug as desired when a vasomotor symptom returns to an uncomfortable level or resumes taking the drug before this point is reached. In some embodiments, the patient takes CPA every other day, every third day, every fourth day, or once a week. In some embodiments, the patient takes CPA consecutively for about 14 days or more, immediately before a period during which no CPA is taken. In some embodiments, the time during which the patient then does not take CPA does not exceed about 14 days, about 30 days, about 40 days, about 50 days, about 60 days, about 2 months, about 3 months, about 4 months, about 5 months, about 6 months, about 1 year or about 2 years. In some embodiments, administration is consecutive for at least sixty days from the start of CPA treatment and then can be intermittent at some time thereafter. In some embodiments, administration is consecutive for about 14 days from the start of CPA treatment and then CPA is administered one day per week, two days per week, three days per week, four days per week, five days per week, six days per week, or seven days per week, or some combination thereof thereafter, as needed to alleviate the vasomotor symptoms. Optimum treatment can vary from patient to patient.

In accordance with the present invention, the patients are treated for vasomotor symptoms with CPA in a dosage of about 15 mg or less per day. In some embodiments, the dosage used is about 1 mg, about 2.5 mg, about 5 mg, about 10 mg, or about 15 mg CPA per day. In some embodiments, CPA is administered in an oral dosage form.

In some embodiments, CPA is administered at a dosage and for a time such that the number of vasomotor symptoms is reduced as compared to the number of vasomotor symptoms prior to the start of treatment. In some embodiments, CPA is administered at a dosage and for a time such that the severity of vasomotor symptoms are reduced. In some embodiments, the number of vasomotor symptoms and the overall severity of the vasomotor symptoms are reduced, as compared to the number and severity of vasomotor symptoms prior to the start of treatment. In some embodiments, treatment is such that vasomotor symptoms become less frequent and hot flash score as defined below is reduced. In some embodiments, treatment is at a dosage and for a time in accordance with the present invention such that a substantial elimination of vasomotor symptoms results.

CPA can be administered to a castrated prostatic cancer patient who experiences any number of vasomotor symptoms per day. In some embodiments, a patient experiencing approximately 3 vasomotor symptoms per day, is treated with a dosage of about 15 mg or less of CPA per day for a time such that the number and/or severity of the vasomotor symptoms are reduced or such that the vasomotor symptoms are substantially eliminated.

Patients who are treated with about 15 mg or less of CPA per day can advantageously achieve alleviation or elimination of vasomotor symptoms. Patients having an average of about 21 vasomotor symptoms per week can also benefit. Moreover, it is recognized that treatment with CPA at a dosage amount in accordance with the present invention to castrated prostatic cancer patients diagnosed by a physician with vasomotor symptoms warranting treatment can also be effective to produce a sufficiently significant result in terms of a decrease in the number of vasomotor symptoms they experience.

Reductions in the number and/or the severity of vasomotor symptoms in patients experiencing at least approximately 3 vasomotor symptoms per day or diagnosed with vasomotor symptoms warranting treatment can be suitable in the treatment range of about 15 mg or less of CPA per day.

An approximate number of vasomotor symptoms is about the average number of vasomotor symptoms experienced over the few days before the start of CPA administration, e.g., over the last three to five days. It could also be about the average number over a longer span of time before the start of administration, e.g., over about twelve weeks. The overall severity distribution of vasomotor symptoms is the approximate percentage of vasomotor symptoms a patient has in each severity category. A reduction in the severity of vasomotor symptoms a patient experiences upon CPA treatment occurs when a greater percentage of vasomotor symptoms are characterized into lower severity categories than in the severity distribution prior to treatment.

A hot flash score is a value that represents the number of hot flashes multiplied by the severity or intensity of the hot flashes. As described by Loprinzi et al., *N. Engl. J. Med.* 331: 347-352 (1994), the hot flash score for a patient is calculated by adding the total number of mild hot flashes, twice the number of moderate hot flashes, three times the number of severe hot flashes, and four times the number of very severe hot flashes experienced in a given day. For an average hot flash score, the number of hot flashes for a number of days can be added and calculated as above, and then divided by the sum of the number of days for which values were included.

In some embodiments, a dosage which provides a sufficiently significant result is one which reduces the number of hot flashes experienced in a patient who has at least approximately 3 hot flashes per day, by more than one hot flash per day. Such a dosage can, of course, be administered to patients who experience fewer than 3 hot flashes per day.

In some embodiments, a dosage which provides a sufficiently significant result in terms of the reduction in number of hot flashes, also reduces the overall severity distribution of any remaining hot flashes. A measure which represents a composite value that takes into account a reduction in number as well as in severity of hot flashes, is a reduction in the hot flash score of a patient. In some embodiments, a dosage of CPA in accordance with the present invention is administered for a duration such that the hot flash score is reduced as compared to the score prior to treatment. In some embodiments, hot flash score decreases by at least about 20% of the score prior to CPA treatment.

It is recognized that typically the hot flash score will reflect a reduction in both the number and severity of hot flashes. In some embodiments, a dosage which may not meet the criteria for a sufficiently significant result in terms of a reduction in number of hot flashes as set forth above, may alternatively meet the definition by about a 20% reduction in hot flash score, in which the reduction in severity compensates for the reduction in number. In some embodiments, CPA is administered at a dosage and for a time sufficient such that the patient has a reduction in hot flash score of greater than 20% of the score prior to CPA treatment.

It is recognized that patients experiencing an approximate number of 3 to 25 or more vasomotor symptoms per day, e.g., 29 per day, can surprisingly achieve significant alleviation or substantial elimination of vasomotor symptoms with the present treatment. Moreover, it is recognized that patients experiencing at least approximately 3 vasomotor symptoms per day, most of which are rated from moderate to severe, who are treated with CPA in accordance with the present invention, can achieve a significant lessening in the overall severity of their vasomotor symptoms.

Administration of CPA can continue for at least as long as is sufficient to achieve a reduction in the number of vasomotor symptoms and, in some embodiments, also in the severity of any remaining vasomotor symptoms. For example, CPA can be administered to a patient having vasomotor symptoms rated as mostly mild in severity until the patients' vasomotor symptoms are substantially eliminated. Also for example, CPA can be administered to a patient having vasomotor symptoms rated as mostly moderate in severity before treatment until any vasomotor symptoms experienced during CPA treatment are rated as mild.

In some embodiments, the treatment term is for 14 days or longer, e.g., about 60 days. In some embodiments, the patient is administered CPA for at least 12 weeks, 6 months, 9 months, one year, two years, 2 to 3 years, or as long as the patient requires treatment.

In some embodiments, a dosage form is administered once per day. In some embodiments, a dosage form is administered twice, three times, four times, five times, six times, or seven times a day or more. In some embodiments, an oral dosage is formulated at about 1 mg CPA. Other amounts, e.g., about 2.5 mg, about 5 mg, about 10 mg, or about 15 mg oral dose of CPA, can be formulated.

In some embodiments, the dosage form is a tablet, pill or a caplet. In some embodiments, the dosage form is a capsule. In some embodiments, the dosage form is a scored, immediate release tablet. In some embodiments, the dosage form is an oral suspension, an oral solution, an oral emulsion or a liquid-filled capsule. The liquid-filled capsule can be filled with a solution, a suspension with solid crystals or an emulsion (a liquid-in-liquid). In some embodiments, the dosage form is formulated for buccal or topical administration.

CPA is formulated into a pharmaceutically acceptable dosage form. These dosage forms include, but are not limited to, tablets, coated tablets, caplets, coated caplets, dragees, capsules, cachets, pellets, pills, powders, granules, liquids, gels, syrups, slurries, suspensions and the like, for oral ingestion; and parenteral dosage forms which include, but are not limited to, solutions, suspensions, emulsions, and dry powder comprising an effective amount of CPA as taught in this invention. Alternatively, CPA can be provided in other dosage forms such as a liquid oral dosage, an injectable depot, an intranasal delivery system or a transdermal delivery system, for example, as a patch. The amount of CPA administered per day in any dosage form provides a blood level of CPA corresponding to that obtained by administration of about 15 mg or less of CPA per day in an immediate release tablet prepared according to Example 1.

For oral administration, CPA can be formulated by combining it with pharmaceutically acceptable inactive agents well known in the art. Pharmaceutical preparations for oral use can be obtained by adding the CPA with one or more pharmaceutically acceptable inactive agents, optionally grinding the resulting mixture, and processing the mixture of granules, after adding additional suitable pharmaceutically acceptable inactive agents, if desired, to obtain tablets or dragee cores.

In some embodiments, the dosage form comprising CPA can be administered in the morning with breakfast, in the afternoon with lunch, in the evening with dinner, or just before bed. The dosage form can be administered with or without food. In some embodiments, there is about a 2-fold enhancement, about a 3-fold enhancement, or about a 4-fold enhancement in CPA efficacy when the dosage form is taken with food compared to when it is taken under fasting conditions. In some embodiments, the efficacy of CPA in the dosage form is similar when taken with or without food. In some embodiments, the CPA is administered approximately the same time each day.

It is also known in the art that CPA can be contained in such formulations with pharmaceutically acceptable disintegrants, binders/diluents/fillers, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, "Modern Pharmaceutics," Banker & Rhodes, Informa Healthcare, 4th ed. (2002); and "Goodman & Gilman's The Pharmaceutical Basis of Therapeutics," McGraw-Hill, New York, 10th ed. (2001) can be consulted.

The amount of CPA in the dosage form can vary. For example, the dosage form can contain about 1-15 mg CPA, about 2.5-15 mg CPA, about 5-15 mg CPA, about 10-15 mg CPA, about 1-2.5 mg CPA, about 1-5 mg CPA, or about 1-10 mg CPA. In some embodiments, the dosage form can contain CPA in an amount of about 1 mg, about 2 mg, about 2.5 mg, about 3 mg, about 4 mg, about 5 mg, about 6 mg, about 7 mg, about 8 mg, about 9 mg, about 10 mg, about 11 mg, about 12 mg, about 13 mg, about 14 mg, or about 15 mg.

As used herein, "inactive agent" refers to a substance that is used in the formulation of pharmaceutical compositions, and, by itself, generally has little or no therapeutic value. Various inactive agents can be used in the invention. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other complications commensurate with a reasonable benefit/risk ratio. In some embodiments, the pharmaceutically acceptable inactive agent can be a surfactant, disintegrant, filler, coating, flavor, color, glidant, lubricant, preservative, antibacterial agent, antioxidant, sorbent, chelating agent, buffering agent, emulsifying and suspending agent, or combinations thereof.

In some embodiments, the dosage form contains a surfactant. In some embodiments, the surfactant is present in an amount of about 0.1% to about 5% (wt/wt), about 0.5% to about 3% (wt/wt), about 1.0% to about 2.0% (wt/wt), or about 1.5% to about 1.8% (wt/wt). Surfactants for use with the present invention can be either ionic or non-ionic. Surfactants for use with the present invention include, but are not limited to, sodium lauryl sulfate, polyoxyethylene-polyoxypropylene block copolymers (e.g., poloxamers), polysorbate 80, sodium dodecyl sulfate, polyoxyethylene alkyl ethers, polyethylene glycol, glycerol, fatty acid esters, polyoxyethylene alkylphenols, polyoxyethylene glycerides, polyoxyethylene sterols, polyoxyethylene sorbitan fatty acid esters, polyglycerol fatty acid esters, salts of bile acids (e.g., taurocholate, glycocholate, cholate, deoxycholate, etc.) which may be combined with lecithin, ethoxylated vegetable oils (e.g., Cremophor® EL, BASF AG, Ludwigshafen am Rhein, Germany), vitamin E tocopherol polyethylene and propylene glycol succinate (e.g., Vitamin E TGPS), and combinations thereof. In some embodiments, the surfactant is sodium lauryl sulfate.

In some embodiments, a surfactant is present in a CPA: surfactant ratio of about 1:0.05 to about 0.1:1 by weight, about 1:0.1 to about 0.1:1 by weight, about 1:0.1 to about 0.1:0.1 by weight, or about 1:1 to about 0.1:1 by weight.

In some embodiments, a surfactant is present in a CPA: surfactant ratio of about 15:1 to about 1:1 by weight, about 10:1 to about 1:1 by weight, about 8:1 to about 1:1 by weight, about 6:1 to about 1:1 by weight, about 4:1 to about 1:1 by weight, or about 2:1 to about 1:1 by weight.

In some embodiments, the dosage form contains a disintegrant. A disintegrant can be considered as any substance, or mixture of substances, added to a solid oral dosage form to facilitate its breakup or disintegration after administration. In some embodiments, the disintegrant is present in an amount of about 2% to about 20% (wt/wt), about 7% to about 15% (wt/wt), or about 8% to about 12% (wt/wt). Disintegrants for use with the present invention include, but are not limited to, crospovidone, sodium starch glycolate, sodium carboxymethyl-cellulose, croscarmellose sodium, carboxymethylcellulose, veegum, alginates, agar, guar, tragacanth, locust bean, karaya, pectin, and combinations thereof. In some embodiments, the disintegrant is crospovidone.

In some embodiments, the dosage form contains a filler. In some embodiments, the filler is present in an amount of about 20% to about 95% (wt/wt), about 40% to about 95% (wt/wt), about 60% to about 90% (wt/wt), or about 70% to about 85% (wt/wt). Suitable fillers for use with the present invention include, but are not limited to, microcrystalline cellulose, sucrose, glucose, mannitol, silicic acid, anhydrous lactose, lactose monohydrate and combinations thereof. In some embodiments, the filler is anhydrous lactose. In some embodiments, the filler is microcrystalline cellulose. In some embodiments, the filler is a combination of anhydrous lactose and microcrystalline cellulose.

In some embodiments, the dosage form contains a glidant. In some embodiments, the glidant is present in an amount of about 0.1% to about 3.0% (wt/wt), about 0.4% to about 2.0% (wt/wt), about 0.6% to about 1.5% (wt/wt), or about 0.8% to about 1.0% (wt/wt). Suitable glidants for use with the present invention include, but are not limited to, colloidal silicon dioxide, talc, starch or tribasic calcium phosphate. In some embodiments, the glidant is colloidal silicon dioxide.

In some embodiments, the dosage form contains a lubricant. A lubricant can be considered as any substance, or mixture of substances, that can prevent adhesion of a dosage form material to the surface of dies and punches, reduce interparticle friction, facilitate the ejection of the dosage from the die cavity, and/or improve the rate of flow of the dosage from particles. In some embodiments, the lubricant is present in an amount of about 0.5% to about 6.0% (wt/wt), about 1.0% to about 4.0% (wt/wt), or about 2.0% to about 3.0% (wt/wt). Suitable lubricants for use with the present invention include, but are not limited to, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, zinc stearate, and combinations thereof. In some embodiments, the lubricant is magnesium stearate. In some embodiments, the lubricant is stearic acid. In some embodiments, the lubricant is a combination of magnesium stearate and stearic acid.

In some embodiments, the dosage form is a tablet comprising about 1 mg, about 2.5 mg, about 5 mg, about 10 mg, or about 15 mg of CPA, a surfactant in an amount of about 0.1% to about 5% (wt/wt), a disintegrant in an amount of about 2% to about 20% (wt/wt), a filler in an amount of about 20% to about 95%, a glidant in an amount of about 0.1% to about 3.0% (wt/wt), and a lubricant in an amount of about 0.5% to about 6.0% (wt/wt). In some embodiments, the surfactant is sodium lauryl sulfate, the disintegrant is crospovidone, the filler is a combination of anhydrous lactose and microcrystalline cellulose, and the glidant is colloidal silicon dioxide.

In some embodiments, the dosage form is a tablet comprising about 1 mg, about 2.5 mg, about 5 mg, about 10 mg, or about 15 mg CPA, a surfactant in an amount of about 1.5% to about 1.8% (wt/wt), a disintegrant in an amount of about 8% to about 12% (wt/wt), a filler in an amount of about 70% to about 85%, a glidant in an amount of about 0.8% to about 1.0% (wt/wt), and a lubricant in an amount of about 2.0% to about 3.0% (wt/wt).

In some embodiments, the CPA in the dosage form is micronized. As used herein, "micronized" refers to particles of a composition that have been reduced to about 25 μm or less in diameter.

As used herein, the term "particle size" refers to particle diameter. Particle size and particle size distribution can be measured using, for example, a Hyac/Royco particle size analyzer, a Malvern particle size analyzer, a Beckman Coulter laser diffraction particle size analyzer, a Shimadzu laser diffraction particle size analyzer, or any other particle size measurement apparatus or technique known to persons of ordinary skill in the art. As used herein, the term "particle diameter" relates to a volumetric measurement based on an approximate spherical shape of a particle. The present invention can also comprise semi-spherical, ellipsoidal, or cylindrical particles without limitation. In addition to encompassing CPA particles of a given size, the present invention is also directed to formulations and dosage forms wherein the distribution of particle sizes of CPA and excipients is controlled. As used herein, a "distribution" refers to the number or concentration (i.e., percentage) of particles having a certain size, or range of sizes, within a given lot, batch, or dosage form of the present invention.

As used herein, a "$D_{50}$" value refers to the particle size of a mixture, and specifically the diameter at which 50% (of the particles) of a composition or mixture have a larger equivalent diameter, and the other 50% of the particles have a smaller equivalent diameter. Thus, $D_{50}$ generally refers to the average particle diameter.

As used herein, a "$D_{90}$" value refers to the particle size of a mixture, and specifically the diameter at which about 90% of all measurable particles have a diameter equal to or less than the $D_{90}$ value, in microns, and about 10% of the measurable particles have a diameter greater than the $D_{90}$ value, in microns.

In some embodiments, the CPA in the dosage form of the present invention has a $D_{90}$ of about 25 microns or less. In some embodiments, the CPA in the dosage form of the present invention has a $D_{90}$ of about 25 microns, about 20 microns, about 15 microns, about 10 microns, or about 5 microns.

As used herein, a "$D_{10}$" value refers to the particle size of a mixture, and specifically the diameter at which about 10% of all measurable particles have a diameter equal to or less than the $D_{10}$ value, in microns, and about 90% of the measurable particles have a diameter greater than the $D_{10}$ value, in microns.

The distribution of particle sizes in a mixture can also be defined by the ratio $D_{10}:D_{50}$, the ratio $D_{10}:D_{90}$, and the ratio $D_{50}:D_{90}$.

As used herein, "dissolution" refers to the process by which CPA dissolves into solution from the pharmaceutical dosage forms of the present invention. The dissolution rate of CPA can be measured using, for example, a USP Type I or Type II Dissolution Apparatus. In some embodiments, the dissolution of CPA from the pharmaceutical dosage forms is measured using a USP Type II Paddle Apparatus containing 0.35% sodium lauryl sulfate in 900 mL water at a paddle speed of 50 rpm. In some embodiments, greater than 75% CPA is released in 30 minutes. In some embodiments, about 80%, about 85%, about 90%, about 95%, or about 100% CPA is released in 30 minutes.

The present invention is further illustrated by the following Examples. These Examples are provided to aid in the understanding of the invention and are not to be construed as a limitation thereof.

EXAMPLES

Example 1

Tablets containing 5 mg, 15 mg and 25 mg of cyproterone acetate were prepared. The formulation of the tablets is shown in Table 1.

TABLE 1

Formulation Composition for 5, 15, and 25 mg Cyproterone Acetate Tablets

| # | Ingredients | mg per unit | mg per unit | mg per unit |
|---|---|---|---|---|
| 1 | Cyproterone Acetate (micronized) | 5.000 | 15.00 | 25.00 |
| 2 | Sodium Lauryl Sulfate, NF | 2.500 | 2.500 | 2.500 |
| 3 | Crospovidone, NF (Polyplasdone ® XL) | 15.00 | 15.00 | 15.00 |
| 4 | Anhydrous Lactose, NF (DT Grade) | 30.00 | 30.00 | 30.00 |
| 5 | Anhydrous Lactose, NF (DT Grade) | 40.75 | 30.75 | 20.75 |
| 6 | Microcrystalline Cellulose, NF (Avicel ® PH-302) | 50.75 | 50.75 | 50.75 |
| 7 | Colloidal Silicon Dioxide, NF (Cab-O-Sil ®) | 1.500 | 1.500 | 1.500 |
| 8 | Magnesium Stearate, NF | 1.500 | 1.500 | 1.500 |
| 9 | Stearic Acid, NF | 3.000 | 3.000 | 3.000 |
| | Total | 150.0 | 150.0 | 150.0 |

A procedure to make cyproterone acetate tablets is described below. The procedure describes the manufacture of 15 mg cyproterone acetate tablets (batch size=140,000) as shown in Table 1, however, the amounts of the various components can be adjusted accordingly to make tablets having about 15 mg or less of cyproterone acetate, for example.

FIG. 1 provides a flow chart, 100, representing a process for preparing 15 mg cyproterone acetate tablets using the ingredients listed in Table 1. Referring to FIG. 1, micronized cyproterone acetate, sodium lauryl sulfate, crospovidone, and anhydrous lactose, 101, were placed into a Collette Gral 75 Liter High Shear Mixer. Residual cyproterone acetate from the bag/container was rinsed with about one scoop full of the anhydrous lactose before the addition to the mixer. The timer on the mixer was set for two minutes and started with mixer speed on "low" and chopper speed on "off," 102. The powder in the mixer was allowed to settle for at least five minutes after the completion of mixing. Following mixing, colloidal silicon dioxide, anhydrous lactose, and microcrystalline lactose, 103, were added to the mixer. The timer on the mixer was set for three minutes and started with mixer speed on "low" and chopper speed on "off," 104.

The blend was discharged into a clean, double polyethylene-lined container. A Russell Finex Compact Sieve was set with a #30 mesh screen and lid and started with the vibrasonic setting "on" and shaker setting "on." The blend was passed through the sieve into a clean, double polyethylene-lined container, 105. The screening process was manually aided for those agglomerated that remained on the screen.

The material was transferred into the mixer. The timer on the mixer was set for one minute. The mixer was started with the mixing speed setting on "low" and the chopper speed setting on "off," 106. Magnesium stearate and stearic acid, 107, were added through a #30 mesh hand screen, 108, directly into the mixer and ensured that it was buried in the blend.

The timer on the mixer was set for thirty seconds. The mixer was started with the mixer speed on "low" and the chopper speed on "off," 109, The blend was discharged into a clean, tared, double polyethylene-lined container.

The blend was then subjected to tablet compression, 110, to yield the cyproterone acetate tablets of the present invention, 111. The tablet compression guidelines are listed below.

| TABLET COMPRESSION GUIDELINES | | | |
|---|---|---|---|
| Tablet Weight: 150 mg (Average of 10 Tablets: 142 mg to 185 mg) (Individual Tablet: 138 mg to 162 mg) | Tablet ID UP: Scored Tablet ID Low: Plain | Friability: Tablet Loss Not More Than 1.0% | Tablet Thickness: 0.119" (0.105"- 0.133") (Average of 10 Tablets) |
| Tablet Hardness: 10.0 kp (Average of 10 Tablets: 6.0 kp to 14.0 kp) (Individual Tablet: 5.0 kp to 15.0 kp) | Tablet Color: White | Tablet Size: 9/32" Round, flat-faced, beveled-edge | Compression Speed: (20 RPM to 80 RPM) Target: 60 RPM |

Example 2

Figure 2:
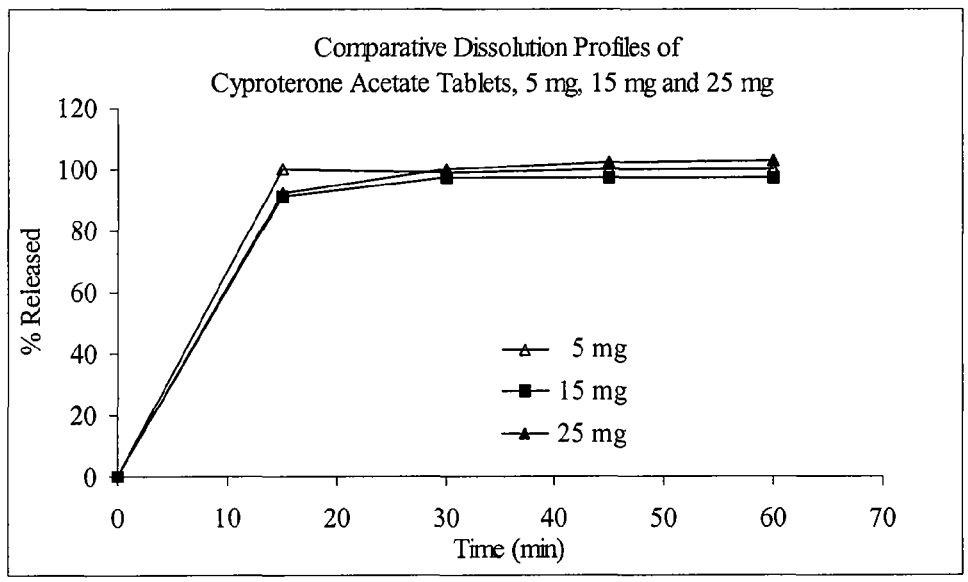
FIG. 2 shows the dissolution data and profiles of 5 mg, 15 mg and 25 mg cyproterone acetate tablets of the present invention.

Cyproterone acetate tablets, 5 mg, 15 mg and 25 mg, were prepared by the process of Example 1. The dissolution profiles were determined using a USP Type II Paddle Apparatus containing 0.35% SLS in 900 mL water at a paddle speed of 50 rpm. These results are listed in FIG. 2.

Example 3

A randomized, multicenter, placebo-controlled clinical trial was conducted in the United States and Canada to study the safety and efficacy of 5, 15, and 25 mg/day cyproterone acetate for the treatment of hot flashes following surgical or medical castration of prostate cancer patients.

The inclusion criteria included male (>18 years) prostate cancer patients who have undergone bilateral orchiectomy or have used or are using LHRH analogue drug(s) (e.g., Lupron®, Zoladex®, Aberelix®), and have complained of bothersome hot flashes as defined by the occurrence of at least 3 moderate to severe hot flashes per day or 21 per week at baseline. Hot flashes were present for at least 1 month prior to study entry.

A total of 362 subjects were randomized and 351 subjects were treated to achieve approximately 75 analyzable subjects per arm. A total of 121 clinical sites in the United States and Canada participated in this Phase 2 study with 77 sites enrolling at least one subject. The overall study duration for each subject was approximately 19 weeks, which included a screening period of up to 4 weeks, a one-week placebo run-in period, a 12-week double-blind period, and a follow-up telephone call two weeks after the last dose of study medication.

After providing informed consent on the first day of the screening period, all subjects had medical and hot flash history recorded, a physical examination, a chest x-ray and Doppler to assess known thromboembolic risk factors, an ECG to evaluate cardiac risks, and clinical laboratory evaluations. Once all results of tests conducted during the screening period were obtained, subjects who met all of the inclusion criteria and none of the exclusion criteria were eligible to enter the one-week, single-blind, placebo run-in period. Subjects who had at least 21 (average of 3 per day) moderate to severe hot flashes during the placebo run-in period and who continued to meet all eligibility criteria were invited to participate in the 12-week double-blind period and were randomized equally to one of the four double-blind treatment groups: CPA 5, 15, or 25 mg/day or placebo. After beginning study medication, subjects returned for study visits at weeks 2, 4, 8, and 12. Two weeks after the final treatment visit, a telephone follow-up call was conducted to record and evaluate adverse events ("AE"s) since the last study visit.

Each subject received one tablet daily, which was administered orally. All tablets were blinded and identical in appearance. The formulation used in this study was an immediate release product containing 5, 15, or 25 mg of CPA. The CPA tablets are described in Example 1. The dosage form for the CPA used in this study was an identical, blind, modified oval, scored, immediate release oral tablet for each strength, consisting of cyproterone acetate, lactose, microcrystalline cellulose, crospovidone, sodium lauryl sulfate, silicon dioxide, magnesium stearate, and stearic acid. Placebo tablets included the same constituents but without CPA and were identical in appearance to the active tablets.

During the single-blind placebo run-in period, subjects received one medication bottle containing a one week+2 day supply (9 tablets total) of single-blind placebo tablets and a copy of the Subject Information Sheet. Subjects were instructed to take one tablet each morning by mouth, preferably with a meal, at approximately the same time each day. Subjects were not made aware that they were receiving placebo.

Following randomization at Visit 2, all enrolled and eligible subjects were randomized equally to one of four treatment groups (CPA 5, 15, 25 mg, or placebo) and received the study medication on the same day. At treatment visits 0, 4, and 8 weeks following initiation, each subject received one medication bottle containing a one-month supply+7 (35 tablets total) of double-blind placebo tablets and a copy of the Subject Information Sheet. Subjects were instructed to take one tablet each morning by mouth, preferably with a meal, at approximately the same time each day.

This study was designed to evaluate three doses of CPA (5 mg, 15 mg, and 25 mg) for the treatment of hot flashes in prostate cancer patients. Observation of a reduction in the frequency and severity of hot flashes was considered a reasonable and reliable indicator of the efficacy of active treatment.

The primary measure of efficacy was the change in weekly frequency and weekly average severity of moderate to severe hot flashes from the placebo run-in period to the final week of treatment. Other secondary efficacy evaluations included the change in the weekly severity of all hot flashes from the placebo run-in period to the final week of treatment as well as the proportion of subjects who experienced total elimination of all hot flashes.

The demographics and baseline characteristics of the patients who were treated in the study are shown in Table 2.

TABLE 2

Subject Demographics and Baseline Characteristics

| | CPA 5 mg (N = 77) | CPA 15 mg (N = 95) | CPA 25 mg (N = 86) | Placebo (N = 80) | Total (N = 338) |
|---|---|---|---|---|---|
| Race | | | | | |
| African-American | 15 (19.5%) | 11 (11.6%) | 9 (10.5%) | 6 (7.5%) | 41 (12.1%) |
| Asian | 0 (0.0%) | 0 (0.0%) | 1 (1.2%) | 0 (0.0%) | 1 (0.3%) |
| Caucasian | 61 (79.2%) | 79 (83.2%) | 72 (83.7%) | 72 (90.0%) | 284 (84.0%) |
| Hispanic | 1 (1.3%) | 5 (5.3%) | 3 (3.5%) | 0 (0.0%) | 9 (2.7%) |
| Other | 0 (0.0%) | 0 (0.0%) | 1 (1.2%) | 2 (2.5%) | 3 (0.9%) |
| Age (yrs) | | | | | |
| N | 77 | 95 | 86 | 80 | 338 |
| Mean (Std) | 73.5 (9.09) | 71.3 (9.32) | 72.2 (8.08) | 72.5 (9.38) | 72.3 (8.98) |
| Median | 73.4 | 71.8 | 72.5 | 74.3 | 72.9 |
| (Min, Max) | (42.6, 89.1) | (46.8, 90.3) | (57.0, 88.4) | (52.8, 91.0) | (42.6, 91.0) |
| Weight (lbs) | | | | | |
| N | 77 | 95 | 86 | 80 | 338 |
| Mean (Std) | 200.3 (35.04) | 201.5 (32.69) | 196.7 (27.39) | 196.4 (33.87) | 198.8 (32.22) |
| Median | 197.0 | 199.0 | 194.0 | 189.0 | 196.0 |
| (Min, Max) | (142.0, 297.0) | (126.0, 285.0) | (135.0, 277.0) | (127.0, 320.0) | (126.0, 320.0) |
| Body Mass Index (kg/m$^2$) | | | | | |
| N | 77 | 95 | 86 | 80 | 338 |
| Mean (Std) | 29.1 (4.73) | 29.7 (4.12) | 29.0 (3.61) | 29.0 (4.59) | 29.2 (4.26) |
| Median | 28.0 | 29.3 | 29.0 | 28.3 | 28.8 |
| (Min, Max) | (20.1, 40.4) | (19.8, 40.3) | (19.0, 39.0) | (18.8, 41.6) | (18.8, 41.6) |
| Systolic Blood Pressure (mmHg) | | | | | |
| N | 77 | 95 | 86 | 80 | 338 |
| Mean (Std) | 131.1 (16.74) | 132.3 (16.05) | 131.9 (15.25) | 130.9 (14.75) | 131.6 (15.66) |
| Median | 130.0 | 132.0 | 130.0 | 132.0 | 130.0 |
| (Min, Max) | (100.0, 175.0) | (100.0, 184.0) | (90.0, 170.0) | (98.0, 170.0) | (90.0, 184.0) |
| Diastolic Blood Pressure (mmHg) | | | | | |
| N | 77 | 95 | 86 | 80 | 338 |
| Mean (Std) | 75.1 (8.88) | 76.9 (9.07) | 76.7 (9.28) | 76.3 (8.92) | 76.3 (9.03) |
| Median | 74.0 | 78.0 | 78.0 | 76.0 | 77.0 |
| (Min, Max) | (50.0, 92.0) | (52.0, 100.0) | (55.0, 99.0) | (46.0, 96.0) | (46.0, 100.0) |

Figure 3:
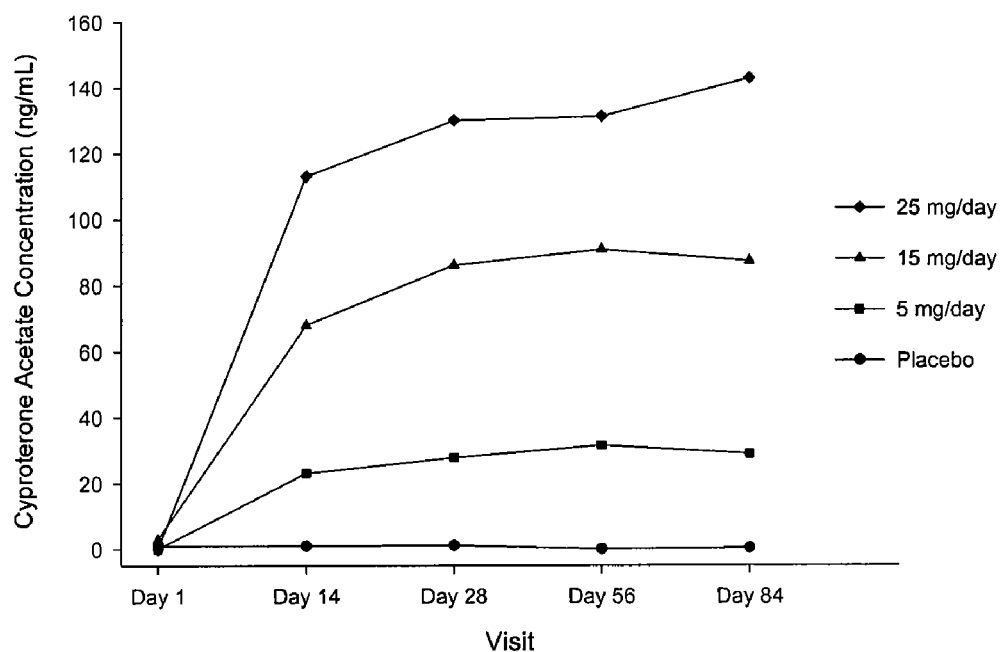
FIG. 3 shows a comparison of the mean cyproterone acetate and 15β-OH cyproterone acetate concentrations by treatment and visit in a castrated prostatic cancer patient administered 5 mg, 15 mg and 25 mg of cyproterone acetate per day.
Figure 3:
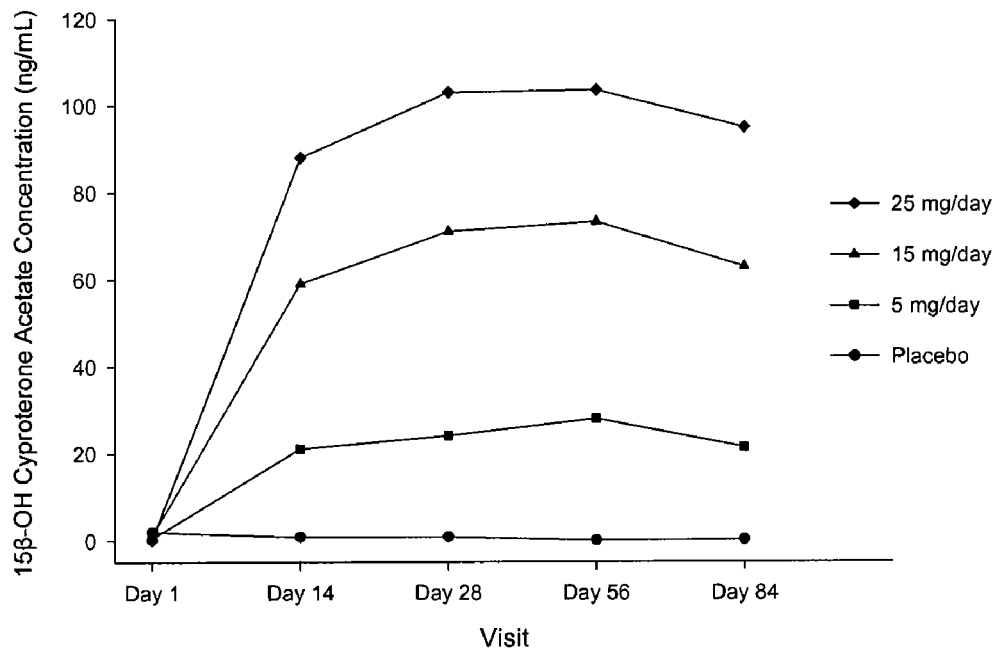

FIG. 3 depicts schematically the analysis of cyproterone acetate and 15β-OH cyproterone acetate (a breakdown product of cyproterone acetate that contributes to the effectiveness of the drug) concentration in the patients who were treated. All three doses, 5 mg/day, 15 mg/day and 25 mg/day, exhibit a dose proportional response.

Figure 4:
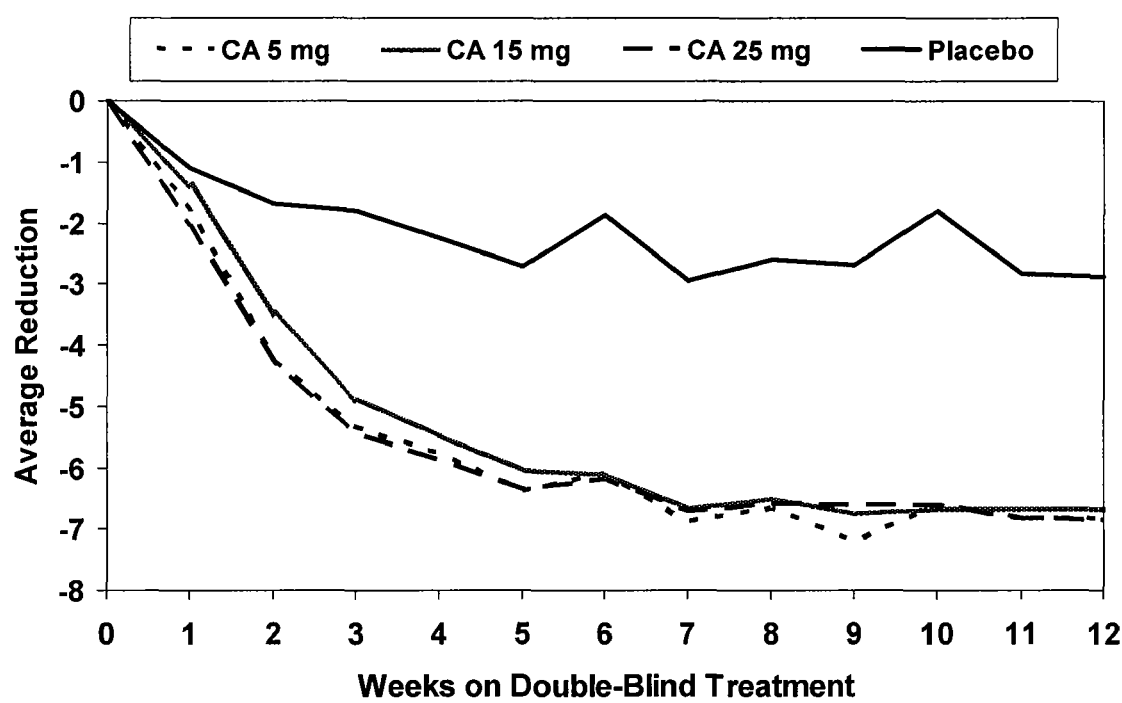
FIG. 4 shows a comparison of the reduction in average daily number of moderate to severe hot flashes in a castrated prostatic cancer patient administered 5 mg, 15 mg and 25 mg of cyproterone acetate per day.
Figure 5:
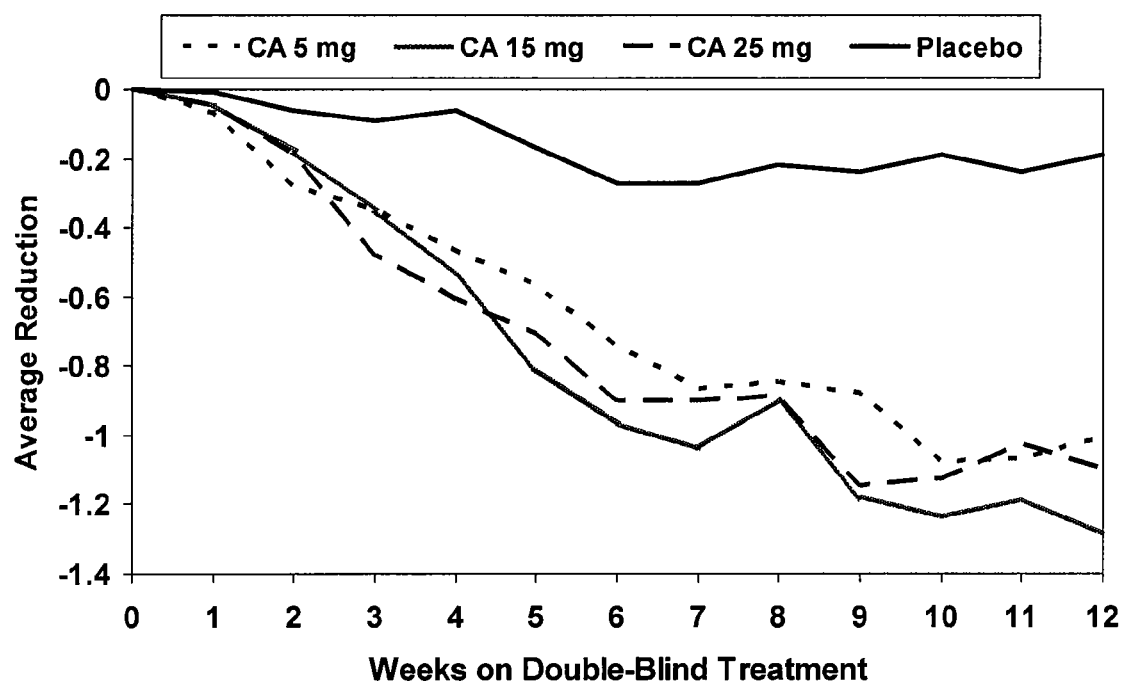
FIG. 5 shows a comparison of the reduction in average severity of hot flashes in a castrated prostatic cancer patient administered 5 mg, 15 mg and 25 mg of cyproterone acetate per day.

Table 3 summarizes the findings associated with analysis of the change from baseline to end-of-treatment for the total weekly frequency of moderate to severe hot flashes in the patients who were treated. All three treatment groups demonstrated a statistically significant reduction in the total weekly frequency of moderate to severe hot flashes over placebo. Compared to placebo, the 5 mg/day CPA group experienced 23.08 fewer moderate to severe hot flashes; while the 15 mg/day and 25 mg/day CPA groups experienced 27.66 and 28.75 fewer moderate to severe hot flashes, respectively. FIG. 4 depicts schematically the reduction from baseline in average daily number of moderate/severe hot flashes.

TABLE 3

Primary Outcome Analysis: Total Weekly Moderate to Severe Hot Flash Frequency: Change from Baseline (Day 0) to End-of-Treatment (Day 84)

| Treatments | N | Baseline | LS Mean Change* | Standard Error | Difference** | P-Value*** |
|---|---|---|---|---|---|---|
| CPA 5 mg | 77 | 57.68 | −40.47 | 3.143 | −23.08 | <.0001 |
| CPA 15 mg | 95 | 50.92 | −45.05 | 2.724 | −27.66 | <.0001 |
| CPA 25 mg | 86 | 50.97 | −46.14 | 2.992 | −28.75 | <.0001 |
| Placebo | 80 | 54.41 | −17.39 | 3.064 | | |

*Change = Change in Total Weekly Moderate to Severe Hot Flash Frequency (Day 0 to Day 84 [or End-of-Treatment]).
**Difference = Difference between active treatment group and matching placebo.
***P-Value: Significance between active treatment group and matching placebo was tested on raw data analysis.

Analysis of the change from baseline to end-of-treatment for the weekly average severity of moderate to severe hot flashes in the patients who were treated are presented in Table 4. All three treatment groups demonstrated a statistically significant reduction in the weekly average severity of moderate to severe hot flashes over placebo. Compared to placebo, the 5 mg/day CPA group experienced a reduction in the average severity of moderate to severe hot flashes of 0.86 units; while the 15 mg/day and 25 mg/day CPA groups experienced a reduction in average severity of 1.13 units and 0.94 units, respectively, using a 4-point scale.

TABLE 4

Primary Outcome Analysis: Weekly Average Severity of Moderate to Severe Hot Flashes: Change from Baseline (Day 0) to End-of-Treatment (Day 84)

| Treatments | N | Baseline | LS Mean Change* | Standard Error | Difference** | P-Value*** |
|---|---|---|---|---|---|---|
| CPA 5 mg | 77 | 2.24 | −1.06 | 0.134 | −0.86 | <.0001 |
| CPA 15 mg | 95 | 2.20 | −1.33 | 0.116 | −1.13 | <.0001 |
| CPA 25 mg | 86 | 2.21 | −1.14 | 0.128 | −0.94 | <.0001 |
| Placebo | 80 | 2.18 | −0.20 | 0.131 | | |

*Change = Change in Weekly Average Severity of Moderate to Severe Hot Flashes (Day 0 to Day 84 [or End-of-Treatment]).
**Difference = Difference between active treatment group and matching placebo.
***P-Value: Significance between active treatment group and matching placebo was tested on raw data analysis.

Table 5 summarizes the proportion of subjects within each treatment group who experienced total elimination of all hot flashes over the duration of the study. The proportion of subjects on placebo who experienced total elimination of all hot flashes was 1.25% (1 subject out of 80). The proportion was significantly higher for all three active treatment groups. The 5 mg/day CPA group had a proportion of 27.27% (21 subjects out of 77); the 15 mg/day CPA group had a proportion of 32.63% (31 subjects out of 95); and the 25 mg/day CPA group had a proportion of 36.05% (31 subjects out of 86). Subjects within the active treatment groups demonstrated a significant difference compared to placebo for total elimination of all hot flashes.

TABLE 5

Secondary Outcome Analysis: Proportion of Subjects with Total Elimination of Moderate to Severe Hot Flashes

| | Did the subject experience total elimination of all moderate to severe hot flashes? | |
|---|---|---|
| | No | Yes |
| Placebo | 79 (98.75%) | 1 (1.25%) |
| CPA 5 mg | 56 (72.73%) | 21 (27.27%) |
| CPA 15 mg | 64 (67.37%) | 31 (32.63%) |
| CPA 25 mg | 55 (63.95%) | 31 (36.05%) |

Table 6 summarizes the findings associated with analysis of the change from baseline to end-of-treatment for the weekly average frequency of all hot flashes in the patients who were treated. All three treatment groups demonstrated a statistically significant reduction in the weekly average frequency of all hot flashes over placebo. Compared to placebo, the 5 mg/day CPA group experienced a reduction in the average frequency of hot flashes of 27.73 units; while the 15 mg/day and 25 mg/day CPA groups experienced a reduction in average frequency of 32.69 units and 33.93 units, respectively.

TABLE 6

Primary Outcome Analysis: Weekly Average Frequency of All Hot Flashes: Change from Baseline (Day 0) to End-of-Treatment (Day 84)

| Treatments | N | Baseline | LS Mean Change* | Standard Error | Difference** | P-Value*** |
|---|---|---|---|---|---|---|
| CPA 5 mg | 77 | 72.10 | −50.67 | 3.472 | −27.73 | <.0001 |
| CPA 15 mg | 95 | 64.12 | −55.63 | 3.024 | −32.69 | <.0001 |
| CPA 25 mg | 86 | 65.63 | −56.87 | 3.311 | −33.93 | <.0001 |
| Placebo | 80 | 72.91 | −22.94 | 3.409 | | |

*Change = Change in Weekly Average Frequency of All Hot Flashes (Day 0 to Day 84 [or End-of-Treatment]).
**Difference = Difference between active treatment group and matching placebo.
***P-Value: Significance between active treatment group and matching placebo was tested on raw data analysis.
Note:
0 sites were pooled into one "super site" due to testing treatment-by-center interaction (<3 subjects in one or more treatment arms).

Table 7 summarizes the findings associated with analysis of the change from baseline to end-of-treatment for the weekly average severity of all hot flashes in the patients who were treated. All three treatment groups demonstrated a statistically significant reduction in the weekly average severity of all hot flashes over placebo. Compared to placebo, the 5 mg/day CPA group experienced a reduction in the average severity of moderate to severe hot flashes of 0.60 units; while the 15 mg/day and 25 mg/day CPA groups experienced a reduction in average severity of 0.78 units and 0.77 units, respectively, using a 4-point scale.

TABLE 7

Secondary Outcome Analysis: Weekly Average Severity of All Hot Flashes: Change from Baseline (Day 0) to End-of-Treatment (Day 84)

| Treatments | N | Baseline | LS Mean Change* | Standard Error | Difference** | P-Value*** |
|---|---|---|---|---|---|---|
| CPA 5 mg | 77 | 2.00 | −0.76 | 0.102 | −0.6 | <.0001 |
| CPA 15 mg | 95 | 1.96 | −0.94 | 0.088 | −0.78 | <.0001 |
| CPA 25 mg | 86 | 1.95 | −0.93 | 0.097 | −0.77 | <.0001 |
| Placebo | 80 | 1.89 | −0.16 | 0.100 | | |

*Change = Change in Weekly Average Severity of All Hot Flashes (Day 0 to Day 84 [or End-of-Treatment]).
**Difference = Difference between active treatment group and matching placebo.
***P-Value: Significance between active treatment group and matching placebo was tested on raw data analysis.
Note:
0 sites were pooled into one "super site" due to testing treatment-by-center interaction (<3 subjects in one or more treatment arms).

This double-blind study incorporating a week-long placebo run-in period followed by 12 weeks of active treatment or placebo demonstrated that 5 mg, 15 mg, and 25 mg doses of CPA significantly reduced the weekly frequency and severity of moderate to severe hot flashes compared to placebo from baseline to the end-of-treatment. For the patients who were treated, the 5 mg/day CPA group had a reduction in the frequency of moderate to severe hot flashes relative to placebo of 23.08. The 15 mg/day CPA group had a frequency reduction of 27.66 and the 25 mg/day CPA group had a frequency reduction of 28.75 over placebo. Additionally, for the secondary analysis of reduction in the average frequency of all hot flashes from baseline to end-of-treatment, all three treatment groups significantly reduced the average frequency compared to placebo.

The average severity of moderate to severe hot flashes was also significantly reduced in all three active treatment groups compared to placebo. For patients who were treated, the 5 mg/day CPA group was able to further reduce the average severity of moderate to severe hot flashes compared to placebo by 0.86, while the 15 mg/day and 25 mg/day also demonstrated reductions of 1.13 and 0.94, respectively. Additionally, for the secondary analysis of reduction in the average severity of all hot flashes from baseline to end-of-treatment, all three treatment groups significantly reduced the average severity compared to placebo.

The results of this trial suggest that all three doses of CPA are effective at treating all hot flashes, including mild, moderate, and severe hot flashes.

The incidence of treatment-emergent AEs reported with a frequency of 3% or greater, by body system, is provided in Table 8 by MedDRA preferred term for all treated subjects. The CPA 5 mg/day group had the fewest proportion of subjects experiencing treatment-emergent AEs followed by the placebo group, the CPA 15 mg/day group, and finally the CPA 25 mg/day group. The results of this trial show that the placebo and the CPA 5 mg/day group had similar adverse event profiles.

Among treatment-emergent AEs that occurred in 3% or more of subjects, several AEs were associated with incidence rates that increased with dose. Gynaecomastia was not reported by subjects in the CPA 5 mg/day group; however, the rate increased to 2.02% in the CPA 15 mg/day group and 4.60% in the CPA 25 mg/day group. Peripheral oedema occurred in 1.23% of subjects in the CPA 5 mg/day group and in 1.01% of the CPA 15 mg/day group. The rate increased to 5.75% in the CPA 25 mg/day group. Dyspnoea occurred in 3.70% of subjects in the CPA 5 mg/day group. The incidence increased to 7.07% in the CPA 15 mg/day group and to 8.05% in the CPA 25 mg/day group. Finally, dizziness occurred in 2.47% of the subjects in the CPA 5 mg/day. The percentage increased to 7.07% in the CPA 15 mg/day group; however, the rate did not continue to increase in the CPA 25 mg/day group but was still higher than the CPA 5 mg/day group at 4.60%.

TABLE 8

Adverse Events: Incidence of Treatment-Emergent Adverse Events Occurring in 3% or More of Subjects

| MedDRA System Organ Class and Preferred Term | CPA 5 mg (N = 81) | | CPA 15 mg (N = 99) | | CPA 25 mg (N = 87) | | Placebo (N = 84) | | Total (N = 351) | |
|---|---|---|---|---|---|---|---|---|---|---|
| | N | % | N | % | N | % | N | % | N | % |
| Infections and infestations | | | | | | | | | | |
| Nasopharyngitis | 3 | 3.70 | 3 | 3.03 | 5 | 5.75 | 2 | 2.38 | 13 | 3.70 |
| Urinary tract infection | 1 | 1.23 | 0 | 0.00 | 3 | 3.45 | 0 | 0.00 | 4 | 1.14 |
| Influenza | 0 | 0.00 | 1 | 1.01 | 3 | 3.45 | 0 | 0.00 | 4 | 1.14 |
| Musculoskeletal and connective tissue disorders | | | | | | | | | | |
| Pain in extremity | 3 | 3.70 | 3 | 3.03 | 0 | 0.00 | 4 | 4.76 | 10 | 2.85 |
| Nervous system disorders | | | | | | | | | | |
| Headache | 3 | 3.70 | 2 | 2.02 | 3 | 3.45 | 1 | 1.19 | 9 | 2.56 |
| Dizziness | 2 | 2.47 | 7 | 7.07 | 4 | 4.60 | 4 | 4.76 | 17 | 4.84 |
| Respiratory, thoracic, and mediastinal disorders | | | | | | | | | | |
| Dyspnoea | 3 | 3.70 | 7 | 7.07 | 7 | 8.05 | 3 | 3.57 | 20 | 5.70 |
| Gastrointestinal disorders | | | | | | | | | | |
| Diarrhoea | 2 | 2.47 | 6 | 6.06 | 3 | 3.45 | 2 | 2.38 | 13 | 3.70 |
| Vomiting | 1 | 1.23 | 0 | 0.00 | 2 | 2.30 | 3 | 3.57 | 6 | 1.71 |
| Constipation | 0 | 0.00 | 6 | 6.06 | 3 | 3.45 | 1 | 1.19 | 10 | 2.85 |
| Nausea | 0 | 0.00 | 2 | 2.02 | 2 | 2.30 | 5 | 5.95 | 9 | 2.56 |
| General disorders and administration site conditions | | | | | | | | | | |
| Fatigue | 1 | 1.23 | 6 | 6.06 | 1 | 1.15 | 3 | 3.57 | 11 | 3.13 |
| Oedema peripheral | 1 | 1.23 | 1 | 1.01 | 5 | 5.75 | 1 | 1.19 | 8 | 2.28 |
| Psychiatric disorders | | | | | | | | | | |
| Depression | 1 | 1.23 | 4 | 4.04 | 1 | 1.15 | 1 | 1.19 | 7 | 1.99 |
| Reproductive system and breast disorders | | | | | | | | | | |
| Gynaecomastia | 0 | 0.00 | 2 | 2.02 | 4 | 4.60 | 2 | 2.38 | 8 | 2.28 |

The incidence of AEs judged to be possibly, likely, or definitely related to study medication reported with a frequency of 3% or greater is presented in Table 9. In the case of constipation, 2 of the 6 cases in the CPA 15 mg group were judged to be related to study medication and all three of the cases in the CPA 25 mg group were judged to be related. For dyspnoea, 4 of the 7 cases in both the 15 mg and 25 mg CPA groups were considered to be related to study medication.

TABLE 9

Adverse Events: Incidence of Treatment-Related Adverse Events Occurring in 3% or More of Subjects

| MedDRA System Organ Class and Preferred Term | CPA 5 mg (N = 81) | | CPA 15 mg (N = 99) | | CPA 25 mg (N = 87) | | Placebo (N = 84) | | Total (N = 351) | |
|---|---|---|---|---|---|---|---|---|---|---|
| | N | % | N | % | N | % | N | % | N | % |
| Gastrointestinal disorders | | | | | | | | | | |
| Constipation | 0 | 0.00 | 2 | 2.02 | 3 | 3.45 | 1 | 1.19 | 6 | 1.71 |
| Respiratory, thoracic, and mediastinal disorders | | | | | | | | | | |
| Dyspnoea | 0 | 0.00 | 4 | 4.04 | 4 | 4.60 | 0 | 0.00 | 8 | 2.28 |

Figure 6:
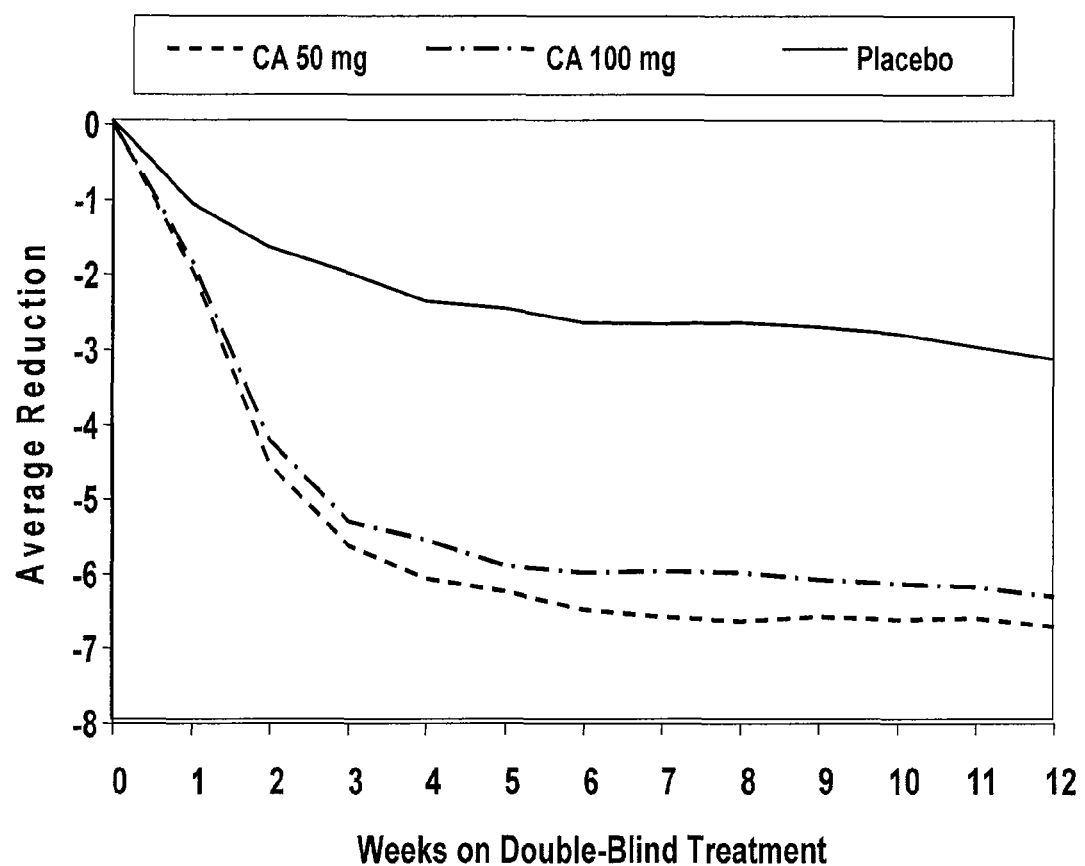
FIG. 6 shows a comparison of the reduction in average daily number of moderate to severe hot flashes in a castrated prostatic cancer patient administered 50 mg and 100 mg of cyproterone acetate per day.
Figure 7:
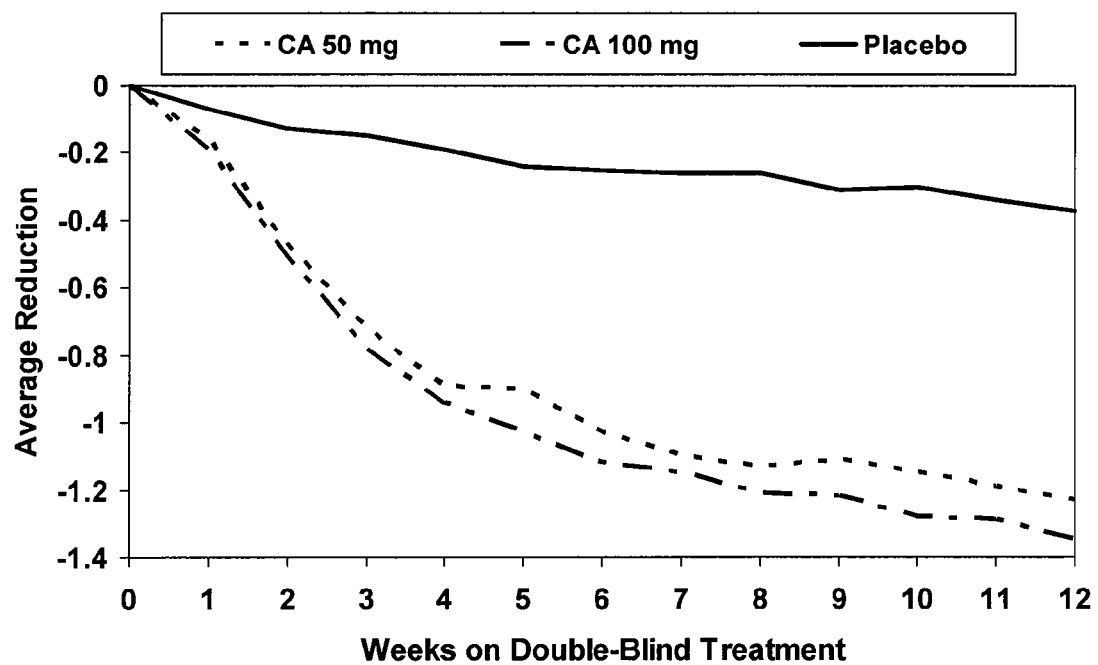
FIG. 7 shows a comparison of the reduction in average severity of hot flashes in a castrated prostatic cancer patient administered 50 mg and 100 mg of cyproterone acetate per day.

The results of this study were compared with results from a prior study in which the efficacy of 50 mg and 100 mg of CPA was investigated. Efficacy data for the 50 mg and 100 mg studies showing a reduction in average daily number of moderate to severe hot flashes, and a reduction in average severity of hot flashes is shown in FIGS. 6 and 7, respectively. A comparison of the percent of patients with complete disappearance of all hot flashes at 12 weeks of treatment across studies is shown in Table 10.

TABLE 10

Percent of All Patients With Complete Disappearance of All Hot Flashes at 12 Weeks/End-of-Treatment

| CPA Dose | N | % With Complete Disappearance |
|---|---|---|
| 100 mg | 236 | 46.0% |
| 50 mg | 236 | 38.5% |
| 25 mg | 86 | 36.1% |
| 15 mg | 96 | 32.3% |
| 5 mg | 80 | 27.5% |
| Placebo (5, 15, 25 mg study) | 220 | 6.6% |
| Placebo (50, 100 mg study) | 84 | 1.2% |

A comparison of the discontinuation rates across studies is shown in Table 11.

TABLE 11

12-Week Double-Blind Discontinuation Rates Across Studies

| Discontinuation | CPA Dose | | | | | Placebo | |
|---|---|---|---|---|---|---|---|
| | 5 mg (N = 81) | 15 mg (N = 99) | 25 mg (N = 87) | 50 mg (N = 246) | 100 mg (N = 245) | 50, 100 mg Study | 5, 15, 25 mg Study |
| Overall | 11 (13.6%) | 15 (15.2%) | 10 (11.5%) | 31 (12.6%) | 42 (17.1%) | 19 (8.2%) | 10 (11.9%) |
| Adverse Event | 2 (2.5%) | 5 (5.1%) | 7 (8.0%) | 13 (5.3%) | 24 (9.8%) | 3 (1.3%) | 2 (2.4%) |
| Withdrew Consent | 8 (9.9%) | 5 (5.1%) | 2 (2.3%) | 7 (2.8%) | 12 (4.9%) | 9 (3.9%) | 7 (8.3%) |

CONCLUSION

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

All publications and patent applications mentioned in this specification are herein incorporated by reference to the same extent as if each individual publication or patent application was specifically and individually indicated to be incorporated by reference.

What is claimed is:

1. A method of treating a vasomotor symptom wherein the vasomotor symptom is hot flashes in a castrated prostatic cancer patient in need of treatment, comprising administering 15 mg or less of cyproterone acetate per day to the patient.

2. The method of claim 1, wherein the patient has at least 3 vasomotor symptoms per day.

3. The method of claim 1, wherein the patient has at least 21 vasomotor symptoms per week.

4. The method of claim 1, wherein the treatment reduces the severity of the vasomotor symptom.

5. The method of claim 1, wherein the treatment reduces the number of vasomotor symptoms per day.

6. The method of claim 1, wherein the patient is treated for at least 14 days.

7. The method of claim 1, wherein the patient is treated for at least 60 days.

8. The method of claim 1, wherein the patient is treated for at least 12 weeks.

9. The method of claim 1, wherein the patient is treated for at least 6 months.

10. The method of claim 1, wherein the patient is treated for 2 to 3 years.

11. The method of claim 6, wherein the patient is treated for at least 14 days consecutively.

12. The method of claim 1, wherein about 1 mg to about 15 mg of cyproterone acetate is administered per day.

13. The method of claim 1, wherein about 5 mg of cyproterone acetate is administered per day.

14. The method of claim 1, wherein about 10 mg of cyproterone acetate is administered per day.

15. The method of claim 1, wherein about 15 mg of cyproterone acetate is administered per day.

16. The method of claim 1, wherein the patient is a chemically castrated prostatic cancer patient.

17. The method of claim 1 wherein the patient is an orchiectomized prostatic cancer patient.

18. The method of claim 1, wherein the administration is oral and is once per day.

19. The method of claim 1, wherein the administration is oral and is divided into 2-5 doses per day.

* * * * *